(12) United States Patent
Messerly et al.

(10) Patent No.: US 7,815,652 B2
(45) Date of Patent: Oct. 19, 2010

(54) SURGICAL FASTENER AND INSTRUMENT

(75) Inventors: Jeffrey David Messerly, Cincinnati, OH (US); Chester O. Baxter, III, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1247 days.

(21) Appl. No.: 11/385,505

(22) Filed: Mar. 21, 2006

(65) Prior Publication Data

US 2007/0225737 A1    Sep. 27, 2007

(51) Int. Cl.
*A61B 17/10* (2006.01)
*A61B 17/08* (2006.01)

(52) U.S. Cl. ........................................ 606/139; 606/151
(58) Field of Classification Search ......... 606/139–159, 606/213–216; 24/454, 456, 570, 910
See application file for complete search history.

(56) References Cited

U.S. PATENT DOCUMENTS

| | | | |
|---|---|---|---|
| 2,832,129 A | 1/1954 | Forster | |
| 5,053,047 A | 10/1991 | Yoon | |
| 5,830,221 A | 11/1998 | Stein et al. | |
| 6,015,416 A | 1/2000 | Stefanchik et al. | |
| 6,036,701 A | 3/2000 | Rosenman | |
| 6,514,263 B1 * | 2/2003 | Stefanchik et al. | 606/144 |
| 6,520,973 B1 * | 2/2003 | McGarry | 606/144 |
| 6,530,932 B1 * | 3/2003 | Swayze et al. | 606/144 |
| 6,613,058 B1 * | 9/2003 | Goldin | 606/144 |
| 6,902,570 B2 * | 6/2005 | Schraft et al. | 606/144 |
| 2002/0026214 A1 | 2/2002 | Tanner et al. | |
| 2003/0208211 A1 * | 11/2003 | Kortenbach | 606/151 |
| 2004/0073237 A1 | 4/2004 | Leinsing | |
| 2004/0153101 A1 | 8/2004 | Bolduc et al. | |

FOREIGN PATENT DOCUMENTS

| | | |
|---|---|---|
| EP | 1254646 | 11/2002 |
| WO | 00/69345 | 11/2000 |
| WO | 03/092509 | 11/2003 |

\* cited by examiner

*Primary Examiner*—(Jackie) Tan-Uyen T Ho
*Assistant Examiner*—Dianne Dornbusch
(74) *Attorney, Agent, or Firm*—Dean L. Garner (57) ABSTRACT

A surgical fastener including a filament formed into a generally helical shape around a fastener axis and having a plurality of coils. The proximal end of the filament has an engagement member and the distal end of the filament has a penetrating tip. The engagement member may be driven to rotate the penetrating tip about the fastener axis such that the coils screw into tissue held in the path of the penetrating tip.

5 Claims, 10 Drawing Sheets

SURGICAL FASTENER AND INSTRUMENT

FIELD OF THE INVENTION

Background of the Invention

The present application relates to surgical fasteners and instruments and, more particularly, to endoscopic surgical fasteners and instruments for approximating and fastening the tissue of a patient.

Surgeons may select from a wide variety of surgical staplers, clip appliers, suturing instruments and other types of instruments to close wounds or to fasten tissues together during a surgical procedure through an open incision or a straight endoscopic port.

Recently there has been significant interest in developing surgical procedures that may be performed through a natural orifice of the patient's body, such as by way of the mouth or anus. For example, some surgeons are developing methods to perform transgastric surgical procedures inside the abdominal cavity. In such procedures, flexible-shaft instruments are used through the working channel of a flexible endoscope that has been inserted through the upper gastrointestinal tract by way of the mouth and passed through an incision in the stomach wall. Among the numerous challenges in performing such procedures is safely closing the transgastric incision by way of the working channel of a flexible endoscope using available tissue fasteners and instruments.

The working channel of a flexible endoscope typically has a diameter in the range of about 2.5 to about 4 millimeters. Current staplers and suturing devices cannot be easily redesigned with smaller diameters to work through such small openings. In addition, performing procedures by way of the working channel does not easily permit using two instruments positioned at different angles with respect to the wound site in order to "pass and catch" a needle and apply sutures.

Accordingly, there is a need for an improved surgical fastener and instrument to approximate and fasten tissue and, particularly, a surgical fastener and instrument that may be used by way of the working channel of a flexible endoscope.

SUMMARY OF THE INVENTION

In one aspect, a surgical fastener is provided and may include a filament formed into a plurality of generally helical coils extending about a fastener axis, wherein a proximal end of the filament includes an engagement member and a distal end of the filament includes a penetrating tip.

In another aspect, a surgical fastening system is provided and may include an end effector including a pair of opposable jaws movable between an open position and a closed position, wherein the opposable jaws are adapted to clamp tissue when in the closed position, a fastener positionable within the end effector, the fastener including a filament formed into a plurality of generally helical coils extending about a fastener axis, wherein a proximal end of the filament includes an engagement member and a distal end of the filament includes a penetrating tip, and a drive element adapted to engage the engagement member and rotate the fastener about the fastener axis to advance the fastener through the end effector.

In another aspect, a surgical instrument for deploying the surgical fastener is provided and may include a shaft that retains a drive element and a closing element. The distal end of the drive element may be operatively engaged to the engagement member of the surgical fastener retained in a loaded position in the distal end of the shaft. The instrument may also include an end effector disposed on the distal end of the shaft and operatively engaged to the distal end of the closing element. The end effector may have a pair of opposable jaws movable between an opened and a closed configuration and adapted to hold tissue along a longitudinal axis in a tissue holding portion of the end effector. Each jaw may have approximately half of a screw thread such that a full screw thread is formed around the longitudinal axis in the tissue clamping portion when the pair of jaws are in the closed configuration. The instrument may further include a handle attached to the proximal end of the shaft and including a first actuator operatively engaged to the proximal end of the closing element for changing the end effector between the opened and closed configurations. The handle may also have a second actuator operatively engaged to the proximal end of the drive element for deploying the surgical fastener. A user may operate the first actuator to hold tissue along the longitudinal axis in the tissue holding portion. The user may operate the second actuator to drive the surgical fastener from the loaded position to a deployed position in the tissue holding portion of the end effector to screw the surgical fastener into tissue held in the tissue holding portion. The user may operate the first actuator to change the end effector to the opened configuration to release the tissue containing the surgical fastener.

Other embodiments of the surgical fastener and instrument will become apparent from the following description, the accompanying drawings and the appended claims.

DETAILED DESCRIPTION OF THE INVENTION

Figure 1:
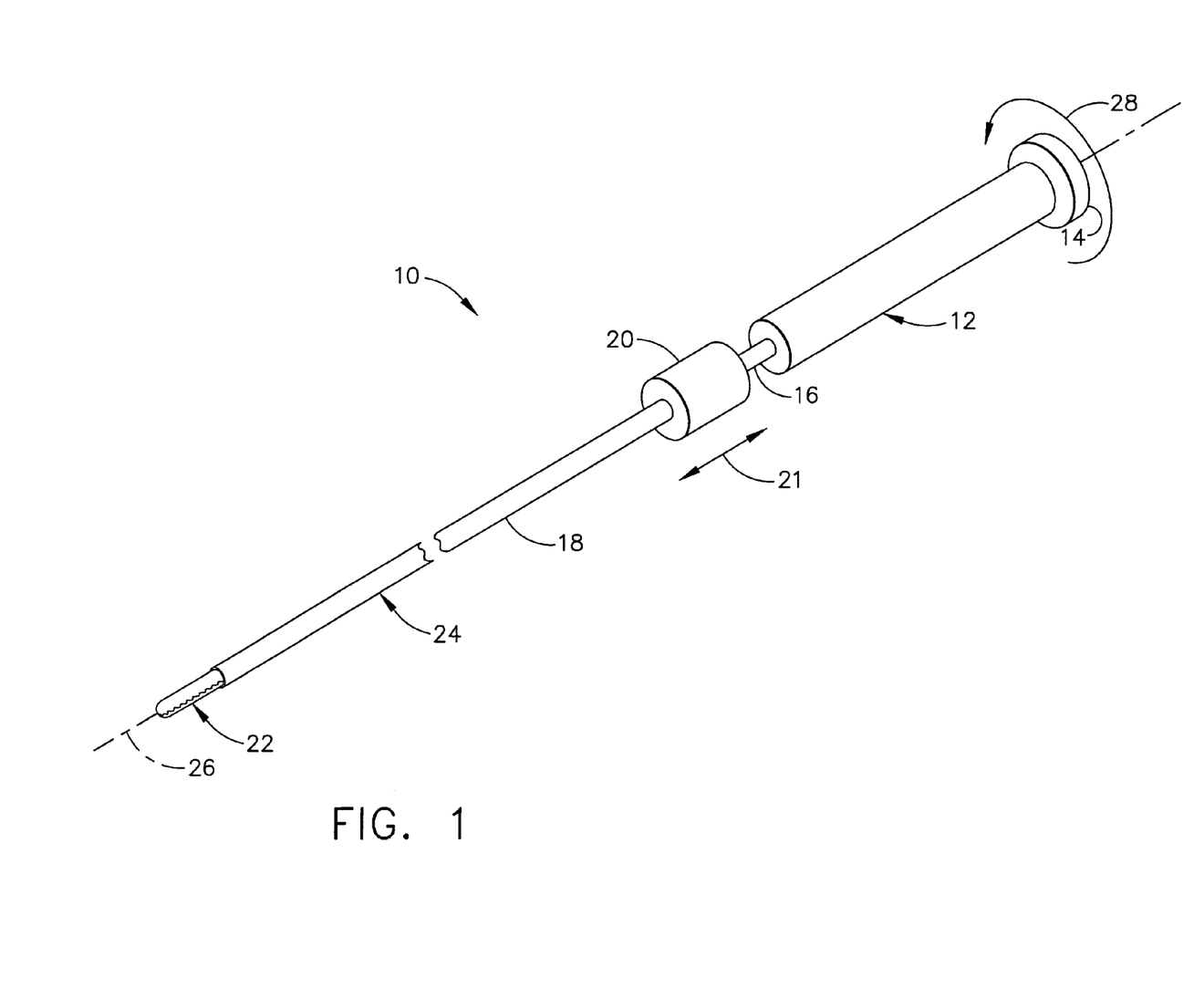
FIG. 1 is an isometric view of a surgical instrument for applying a surgical fastener into the tissue of a patient.
Figure 2:
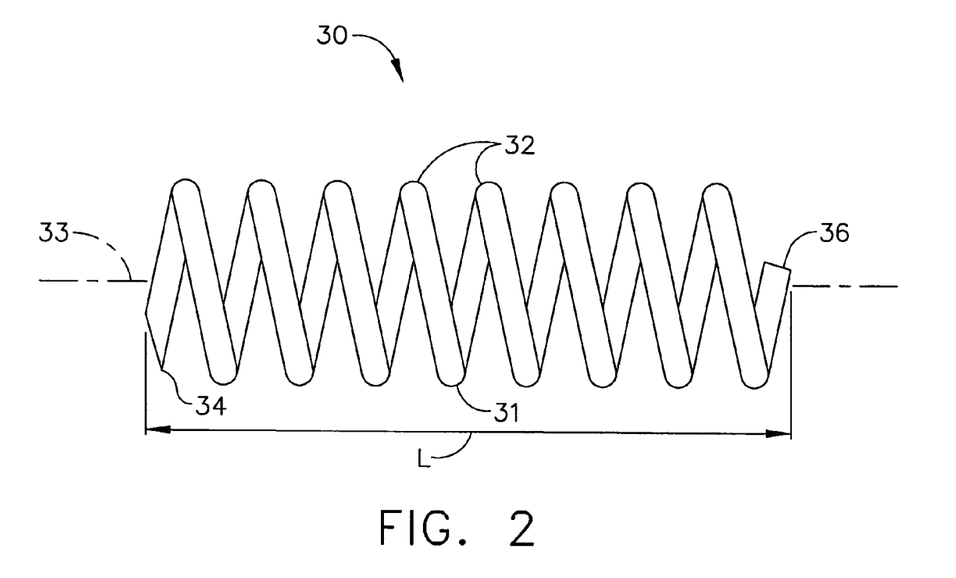
FIG. 2 is a side view of one aspect of a surgical fastener.

FIG. 1 is an isometric view of an exemplary embodiment of a surgical instrument, generally designated 10, for approximating and fastening the tissue of a patient by deploying a surgical fastener 30 such as shown in FIG. 2. Instrument 10 may include a handle 12 having a first actuator 14. Handle 12 may be attached to the proximal end of an elongated shaft 24. Instrument 10 may further include an end effector 22 (shown in a closed configuration) disposed on the distal end of shaft 16. A knob 20 (also referred to as a second actuator) may be attached to the proximal end of a sleeve 18 that is slidably retained on an inner tube 16 of shaft 24. A user may change end effector 22 between an opened and a closed configuration by moving knob 20 along a longitudinal axis 26 as indicated by arrow 21. A user may deploy surgical fastener 30 into the tissue of a patient by rotating actuator 14 about axis 26 as indicated by arrow 28.

Instrument 10 may be used for open and endoscopic surgical procedures, including flexible endoscopic procedures through a natural orifice of the patient's body. Shaft 24 of instrument 10 may be straight, curved, rigid or flexible, and may have a length that is approximately in the range a few centimeters to over one meter. The diameter of shaft 24 may also vary greatly, depending upon the diameter of the surgical fastener 30, and may be in the range of approximately two to twenty millimeters.

Figure 3:
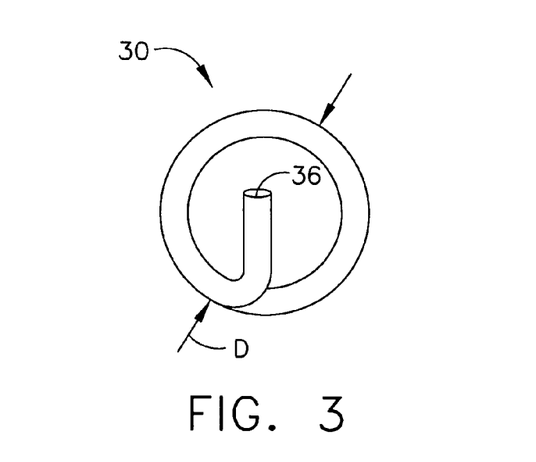
FIG. 3 is an end view of the surgical fastener shown in FIG. 2.

As shown in FIGS. 2 and 3, a first aspect of a surgical fastener 30 may include a filament 31 formed into a generally helical shape around a fastener axis 33 by forming a plurality of coils 32. The proximal end of the fastener 30 may include an engagement member 36 and the distal end may include a penetrating tip 34. As shown in FIG. 3, engagement member 36 may be a tang that is directed radially inward.

The engagement member 36 may be driven to rotate penetrating tip 34 about the fastener axis 33 such that the coils 32 screw into tissue held in the path of the penetrating tip 34. Although FIG. 2 shows fastener 30 having eight coils, those skilled in the art will appreciate that the number of coils 32 may vary. Furthermore, the spacing or pitch between coils 32 may be increased of decreased from that shown in the drawings.

Referring again to FIGS. 2 and 3, the fastener 30 may have an overall length L and an outer diameter D. In one aspect, the length L may be about 5 to about 25 millimeters and the diameter D may be about 2 to about 10 millimeters. In another aspect, the length L may be about 25 to about 200 millimeters and the diameter D may be about 5 to about 50 millimeters.

The fastener 30 may be formed from any of a number of biocompatible and/or bioabsorbable materials, including stainless steel, titanium alloys, a nickel-titanium memory metal (Nitinol), a polymer and an absorbable polymer. The fastener material may be a spring material or a relatively malleable material such that surgical fastener 30 maintains a helical shape when released from the instrument 10. The fastener 30 may be manufactured using any one or a combination of a number of well-known processes, including drawing, winding, extruding, rolling and injection molding.

In cross-section, the filament 31 may have a circular, rectangular or any one of many other geometric shapes. In addition, the cross-sectional size and shape may vary along the length of the fastener 30 in order to provide properties that are most suitable for the surgical application. If the fastener 30 is formed from a titanium alloy (Ti-6Al-4V) wire, for example, the cross-sectional diameter of the wire may be in the range of about 0.2 to about 1.0 millimeters.

The fastener 30 may be coated or treated to facilitate deployment into tissue and/or to improve the surgical outcome. For example, fastener 30 may be coated with a lubricious coating such as a soap, a polymer coating such as Paralene-n that is applied in a vapor deposition process or any one of many other well-known, biocompatible lubricants to reduce friction with interfacing components of instrument 10, thereby lowering the force to deploy fastener 30. The fastener 30 may also be covered with any one of a number of well-known chemical compositions to enhance healing and/or to prevent infection.

Figure 4:
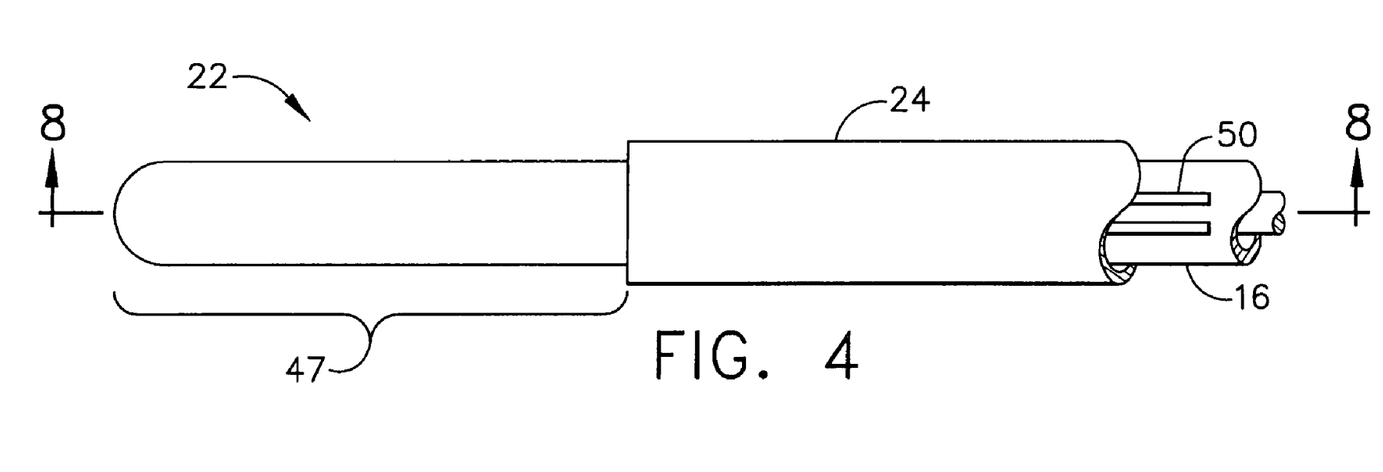
FIG. 4 is a top view of one aspect of an end effector while in a closed configuration.
Figure 5:
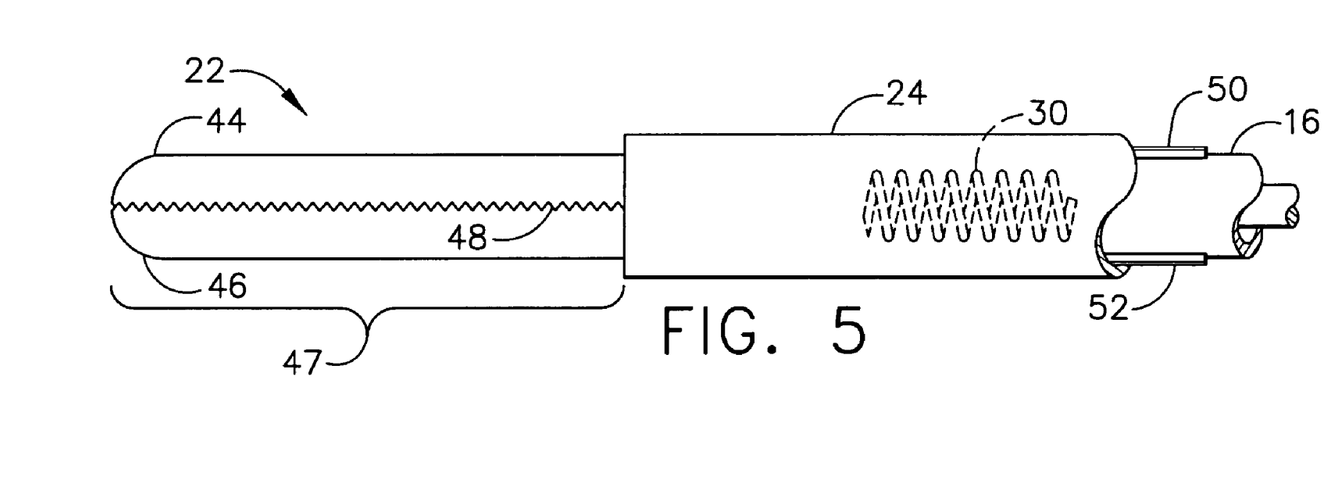
FIG. 5 is a front view of the end effector shown in FIG. 4.
Figure 6:
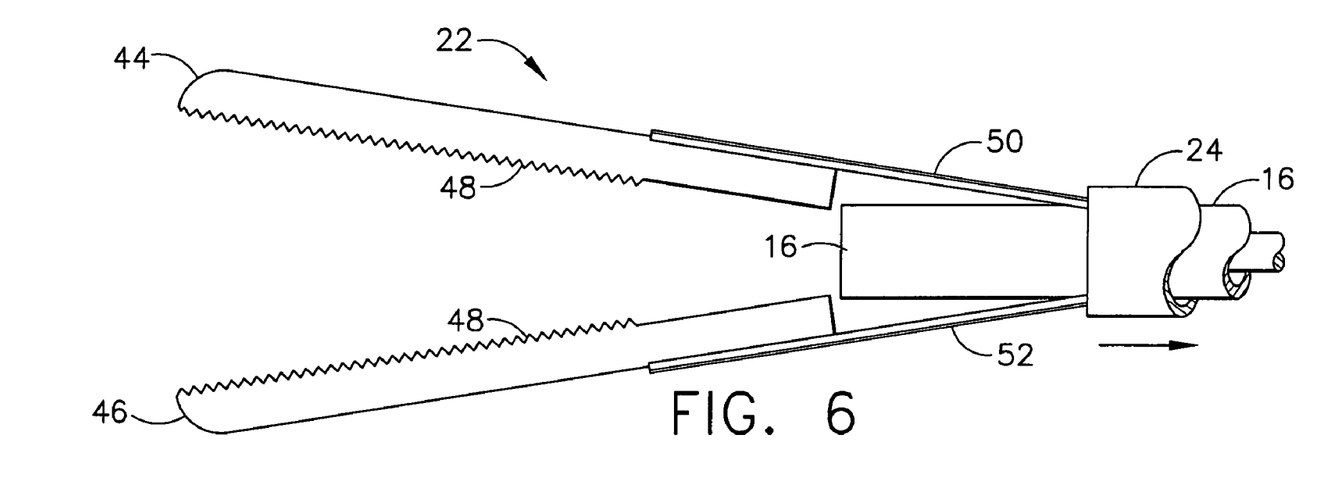
FIG. 6 is a front view of end effector shown in FIG. 4 while in an opened configuration.
Figure 7:
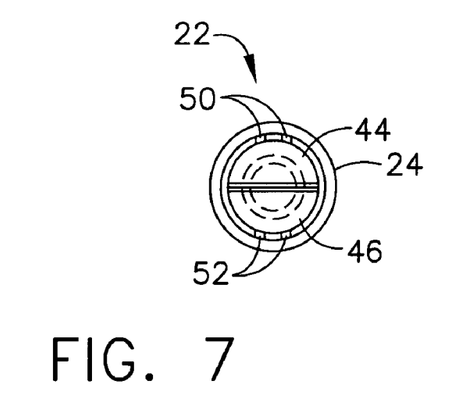
FIG. 7 is an end view of the end effector shown in FIG. 5.

FIG. 4 is a top view, FIGS. 5 and 6 are front views, and FIG. 7 is an end view of a first aspect of an end effector 22 of instrument 10. FIGS. 4, 5, and 7 show end effector 22 in the closed configuration. FIG. 6 shows end effector 42 in the opened configuration.

End effector 22 may include a pair of opposable jaws: first jaw 44 and second jaw 46. Each jaw 44, 46 may include a plurality of interlocking serrations 48 for holding soft tissue in a tissue holding portion 47. A first spring element 50 may attach first jaw 44 and a spring element 52 may attach second jaw 46 to the distal end of inner tube 16, such that jaws 44, 46 are biased to move apart to the opened configuration. A user may advance the sleeve 24 of the instrument 10 in the distal (left) direction to move the jaws 44, 46 to the closed configuration and retract the sleeve 24 in the proximal (right) direction to allow jaws 44, 46 to spring to the opened configuration. In FIG. 5, surgical fastener 30 is shown with dotted lines while in a loaded position inside the distal end of inner tube 16 of the instrument 10.

Figures 8, 9, 10:
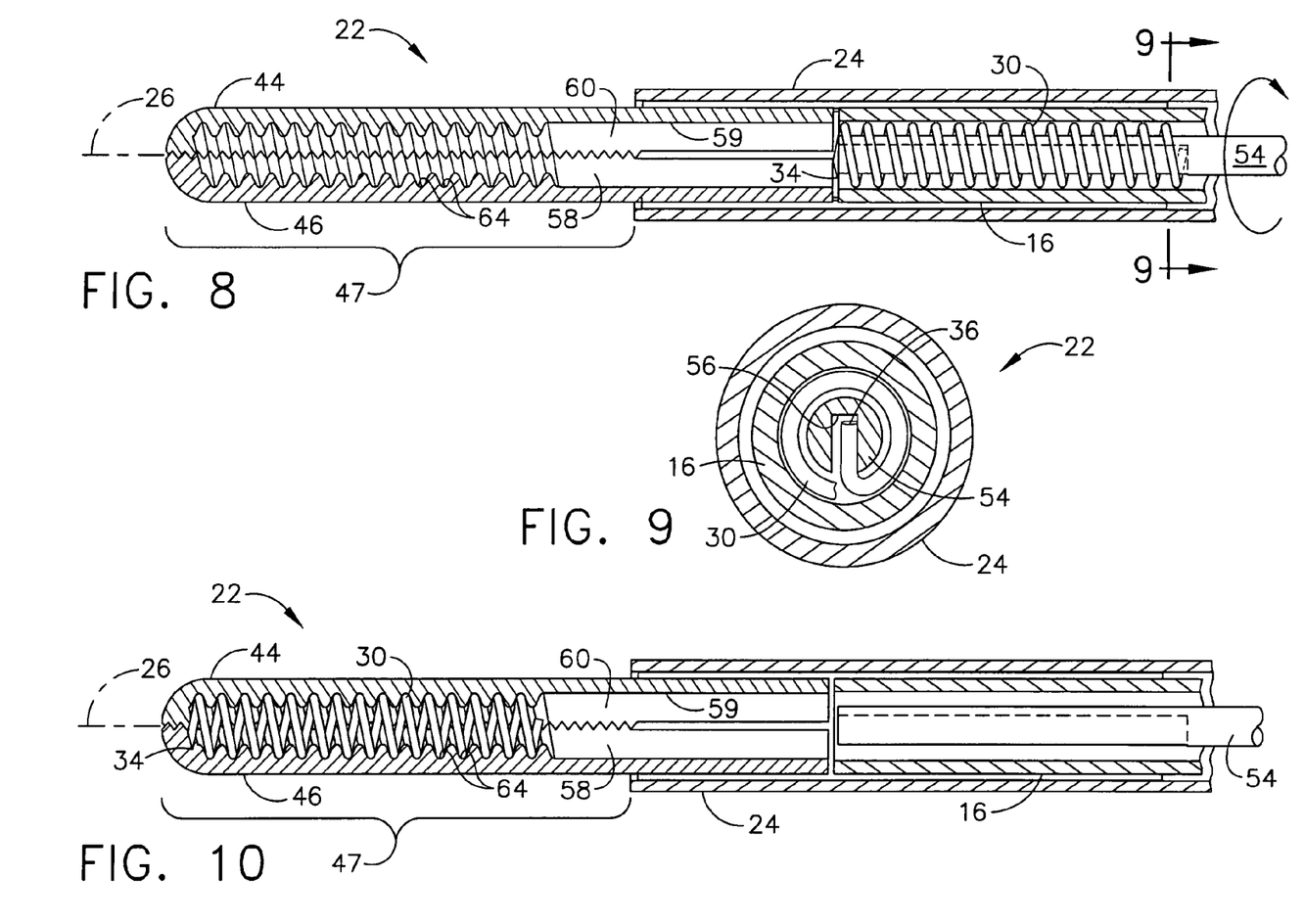
FIG. 8 is a longitudinal sectional view taken at line 8-8 of the end effector of FIG. 4, showing the surgical fastener in a loaded position.
FIG. 9 is a cross-sectional view taken at line 9-9 of the end effector in FIG. 8.
FIG. 10 is a longitudinal sectional view taken at line 8-8 of the end effector shown in FIG. 8, showing the surgical fastener in a deployed position.

FIGS. 8 and 10 are longitudinal sectional views taken at line 8-8 of FIG. 4. FIG. 8 shows surgical fastener 30 in the loaded position and FIG. 10 shows fastener 30 in a deployed position. FIG. 9 is a cross-sectional view taken at line 9-9 of FIG. 8.

Referring first to FIG. 8, a fastener 30 may be retained on the distal end of a drive element 54 inside inner tube 16. The proximal end of drive element 54 may be operatively engaged to second actuator 14 on handle 12 (FIG. 1). As shown in FIG. 9, drive element 54, may include a longitudinal slot 56 adapted to retain the engagement member 36 of the fastener 30, such that fastener 30 may be rotatably driven by drive element 54 about axis 26 while being free to translate distally along axis 26.

When the end effector 22 is in the closed configuration, jaws 44 and 46 may form a chamber 58 that is aligned along axis 26 with inner tube 16. The proximal portion of chamber 58 may include a bore 60 having a smooth bore surface 59. The distal portion of chamber 58 corresponding with tissue holding portion 47 may include a full screw thread 64. Approximately half of a screw thread may be formed into each of jaws 44, 46 in tissue holding portion 47. The diameter of full screw thread 64 may be generally the same or different than the diameter of fastener 30. In one aspect, as shown in FIGS. 8-10, the diameter of full screw thread 64 is generally the same as the diameter of the fastener 30.

Accordingly, when the fastener 30 is in the loaded position as shown in FIG. 8, penetrating tip 34 may be approximately even with the distal end of inner tube 16. To deploy fastener 30, the user may rotate actuator 14 in a first direction. The initial rotation of actuator 14 may rotate a lead screw (not shown) in handle 12, such that drive element 54 and fastener 30 translate distally along axis 26 until penetrating tip 34 is even with the proximal end of threads 64. At that point, further rotation of actuator 14 may cause drive element 54 to rotate only (and not to translate), such that fastener 30 is driven into thread 64 and the tissue held between jaws 44, 46. When the penetrating tip 34 has reached the distal end of the thread 64, the actuator 14 may hit a hard stop in handle 12. When the user retracts sleeve 24 as shown in FIG. 6., jaws 44, 46 may separate and release the tissue with the implanted fastener 30. The user may retract drive element 54 in the proximal direction to the position shown in FIG. 10 by rotating the actuator 14 in a second (reverse of the first) direction.

Alternatively, the instrument 10 may be provided with an electrical motor drive unit (not shown) to operate actuator 14 in order to deploy surgical fastener 30. A user may quickly and controllably deploy surgical fastener 30, for example, by depressing an electrical control switch located on handle 12. The drive unit may be powered by a battery in handle 12 or electrically connected to an external power source.

Surgical fastener 30 may be preformed from a spring material into a first configuration as shown in FIG. 8 and full screw thread 64 in jaws 44, 46 may be configured similarly, such that surgical fastener 30 does not significantly change configuration when driven into full screw thread 64. However, surgical fastener 30 may change to a second configuration (not shown) when released from end effector 22. In one embodiment, the second configuration of fastener 30 may have a smaller diameter and longer length than the first configuration. In another embodiment, the second configuration may have a larger diameter and a shorter length than the first configuration.

Figure 11:
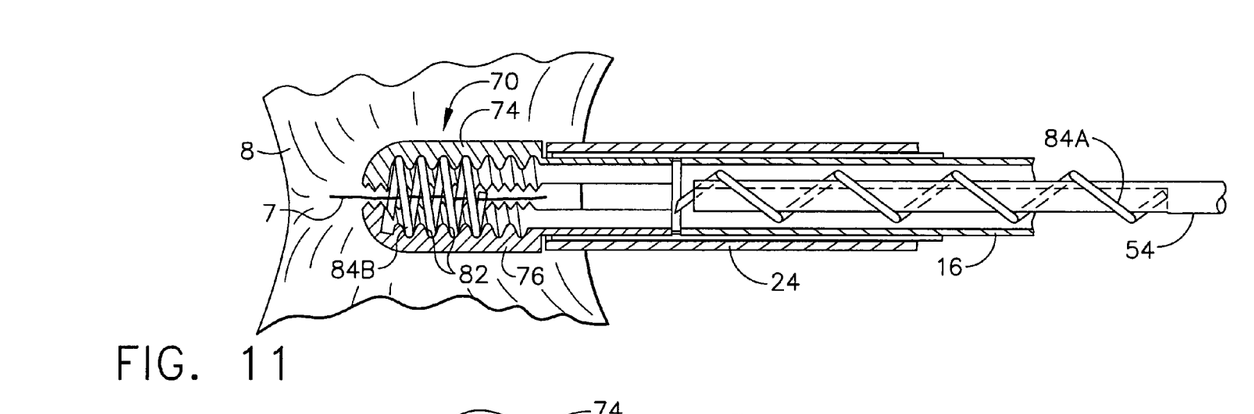
FIG. 11 is a longitudinal sectional view of a second aspect of an end effector while in the closed configuration and clamped onto tissue around an incision, and showing a second aspect of a surgical fastener in the loaded and deployed positions.
Figure 12:
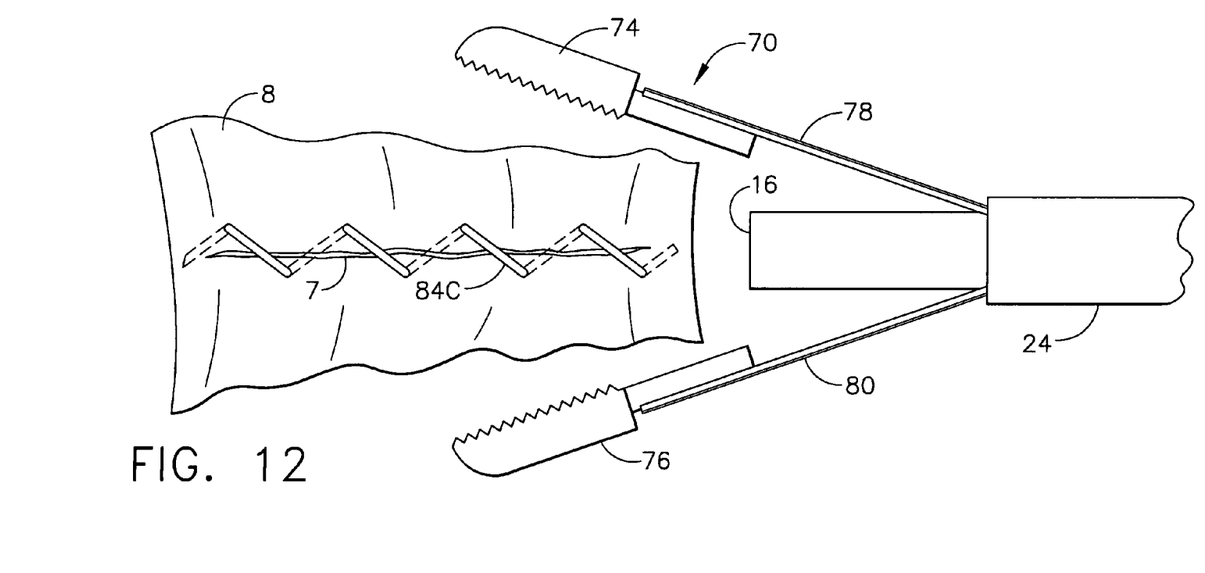
FIG. 12 is a front view of the end effector shown in FIG. 11 while in the opened configuration and showing the surgical fastener implanted into tissue.

As shown in FIGS. 11 and 12, a second aspect of an end effector, generally designated 70, may be used with the instrument 10 of FIG. 1. In FIG. 11, end effector 70 is shown clamped onto tissue 8 about an incision 7. In FIG. 12, end effector 70 is shown released from tissue 8 with the implanted, surgical fastener approximating the edges of incision 7 in close alignment. End effector 70 may include a pair of opposable jaws 74, 76 attached to inner tube 16 by a pair of spring elements 78, 80. The components and operation of instrument 10 for moving jaws 74, 76 and deploying the surgical fastener may be generally similar to that described for the first embodiment shown in FIGS. 4-10. End effector 70, however, may be adapted to deploy a second embodiment of a surgical fastener 84 that is formed from a spring material, such that it may have at least two configurations.

FIG. 11 shows a first configuration 84A of fastener 84 while in the loaded position in inner tube 16. FIG. 11 also shows a second configuration 84B of fastener 84 while in the deployed position in jaws 74, 76. In one embodiment, a single fastener 84 may be driven from the loaded position to the deployed position. In another embodiment, a plurality of surgical fasteners may be stored end-to-end in shaft 16 and may be deployed in a similar manner as shown in FIG. 11.

FIG. 12 shows a third configuration 84C of fastener 84 while implanted in tissue to be approximately the same as first configuration 84A. The first and third configurations, 84A and 84C, may vary somewhat since fastener 84 may be constrained differently when in the loaded position then when implanted in tissue. In general, fastener 84 may have a greater length and a smaller diameter when in the third configuration 84C than when in the second configuration 84B. A benefit of this arrangement is that the movement of fastener 84 from the second to the third configuration while attached to the tissue places a tension on the tissue. This tension may help to approximate (pull together into alignment) the edges of incision 7 to promote proper healing.

As shown in FIG. 11, a full screw thread 82 may be formed into jaws 74, 76. The diameter of thread 82 may be generally greater than the diameter of fastener 84 when in the unconstrained, first configuration. When fastener 84 is driven by drive element 54 into thread 82, fastener 84 may assume the second configuration, while simultaneously screwing into tissue. When fastener 84 is released from jaws 74, 76, fastener 84 may approximately resume the first configuration as shown in FIG. 12, thereby tensioning tissue 8 and approximating incision 7.

Figure 13:
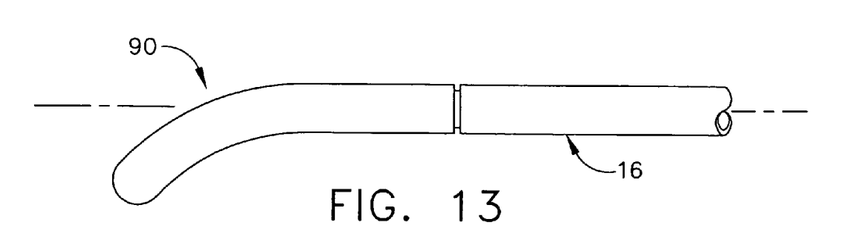
FIG. 13 is a top view of a third aspect of an end effector.
Figure 14:
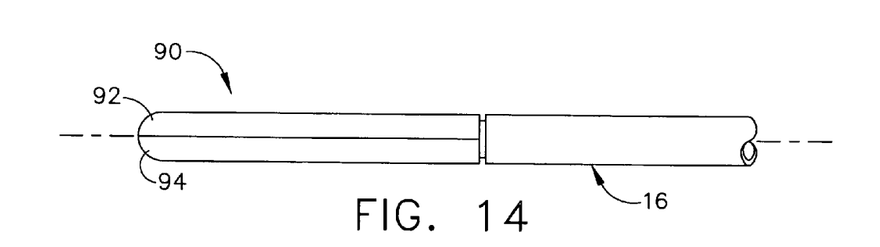
FIG. 14 is a front view of the end effector shown in FIG. 13.
Figure 15:
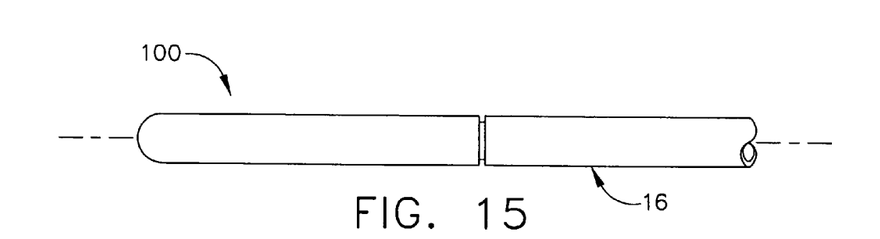
FIG. 15 is a top view of a fourth aspect of an end effector.
Figure 16:
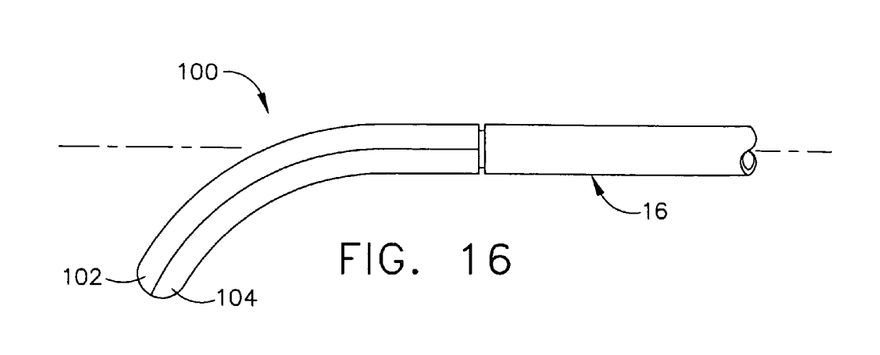
FIG. 16 is a front view of the end effector shown in FIG. 15.

FIGS. 13 through 16 show additional embodiments that exemplify how the end effector may be configured to provide improved access and visibility of tissue for surgical procedures. FIG. 13 is a top view and FIG. 14 is a side view of a third embodiment of an end effector, designated 90, operatively attached to shaft 16. End effector 90 may be similar to either of the first and second embodiments, except that a pair of jaws 92, 94 may have a curved shape in a lateral plane transverse to the plane of jaw movement. FIG. 15 is a top view and FIG. 16 is a side view of a fourth embodiment of an end effector, designated 100, operatively attached to shaft 16. End effector 100 may also be similar to either of the first and second embodiments, except that a pair of jaws 102, 104 may have a curved shape in the plane of jaw movement.

Figure 17:
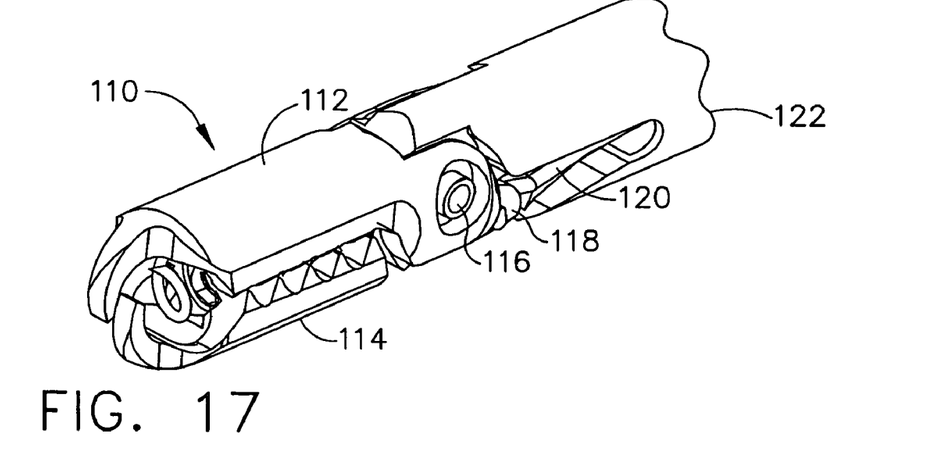
FIG. 17 is an isometric view of a fifth aspect of an end effector while in a closed configuration.
Figure 18:
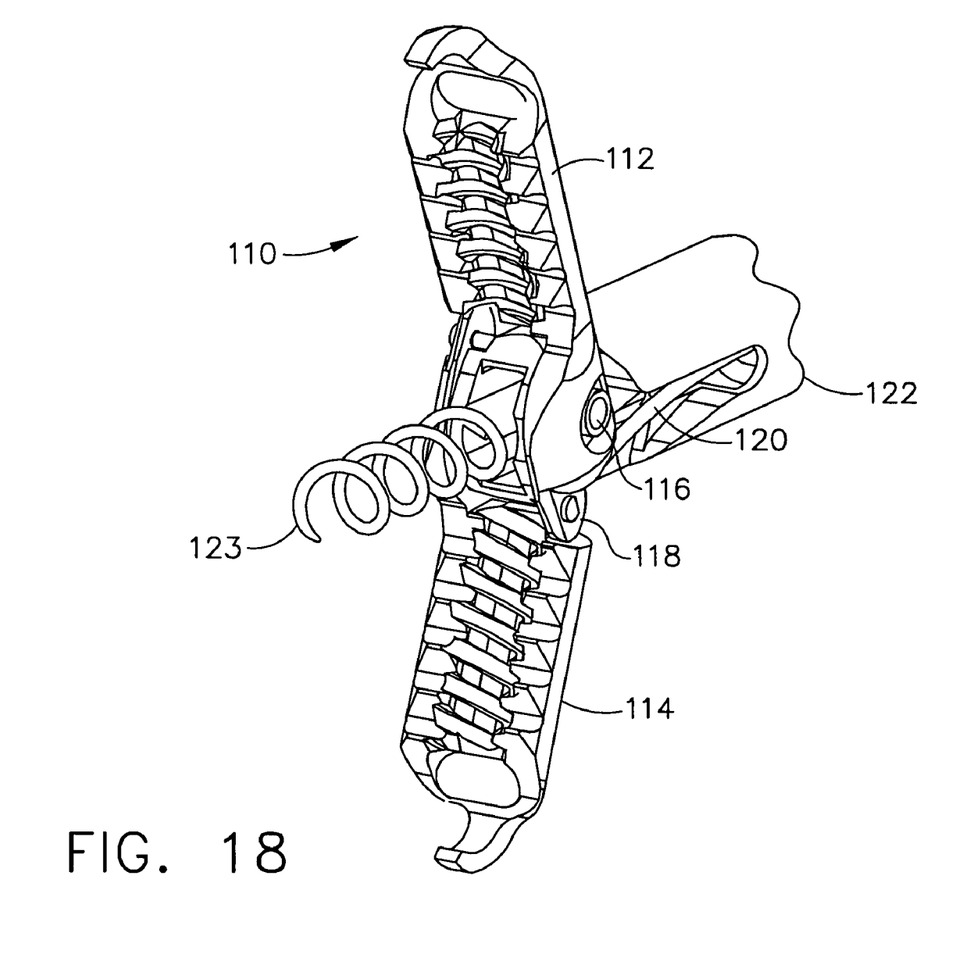
FIG. 18 is an isometric view of the end effector shown in FIG. 17 while in an opened configuration.

FIGS. 17 and 18 are isometric views of another aspect of an end effector, generally designated 110, for applying a surgical fastener in the tissue of a patient. End effector 110 may include a pair of jaws 112, 114 that are attached to the distal end of a shaft 122 by a pair of pivots 116. Each jaw 112, 114 may be operatively engaged by a link element 120 at a connection 118 with link element 120 extending to a handle actuator (not shown) such that a user may open and close the jaws 112, 114. The jaws may be a hermaphroditic design, as is shown in FIGS. 17 and 18, such that assembly of two of the same part design (wherein jaw 112 and jaw 114 are of the same part design, i.e. a common part geometry) accomplishes the desired functions of acquiring tissue and guiding surgical fasteners of the current invention. Use of a hermaphroditic part allows for manufacturing costs and assembly complexities to be minimized. In order for the hermaphroditic jaw pair to appropriately guide the surgical fastener while being attached to the shaft 122 at the same position along the longitudinal axis of the shaft 122, the period of the helical guide or screw thread must be approximately twice the period of the helical surgical fastener as is shown in FIGS. 17 and 18. As is well known in the art, this type of end effector may be particularly useful for dissection of tissue because the actuation stroke may be relatively small and a tissue-spreading force may be provided together with a clamping force. A surgical fastener 123 shown in FIG. 18 may be similar to surgical fastener 30 shown in FIG. 2. The other features, components and method of operation may be similar to that described for the previous embodiments.

The basic design of the surgical fasteners described and claimed herein may be modified for many kinds of surgical procedures. FIGS. 19 through 24 are examples of additional embodiments of the surgical fastener, wherein each embodiment is represented in an unconstrained configuration. When constrained in the surgical instrument prior to deployment, each embodiment may be approximately straight and the coils may have a relatively uniform pitch and diameter.

Figure 19:
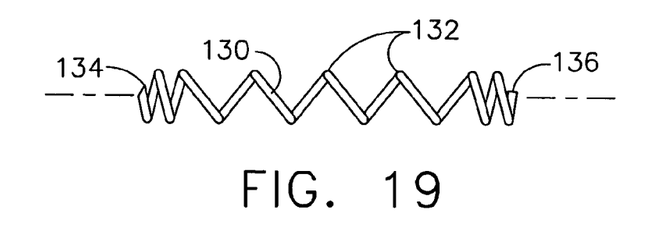
FIG. 19 is a side view of a third aspect of a surgical fastener.

As shown in FIG. 19, a surgical fastener 130 may include a plurality of coils 132 that are spaced closer together on the ends than in the middle portion. This configuration may help to protect adjacent tissues from a penetrating tip 134 and a tang 136 after fastener 130 has been implanted in the tissue.

Figure 20:
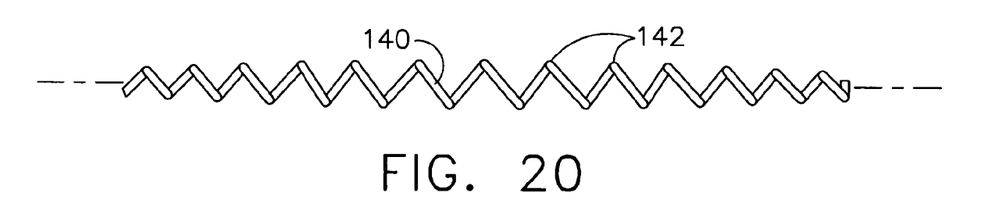
FIG. 20 is a side view of a fourth aspect of a surgical fastener.

As shown in FIG. 20, a surgical fastener 140 may include a plurality of coils 142, wherein the coils 142 in the middle portion have a larger diameter than the coils 142 near the ends of fastener 140.

Figure 21:
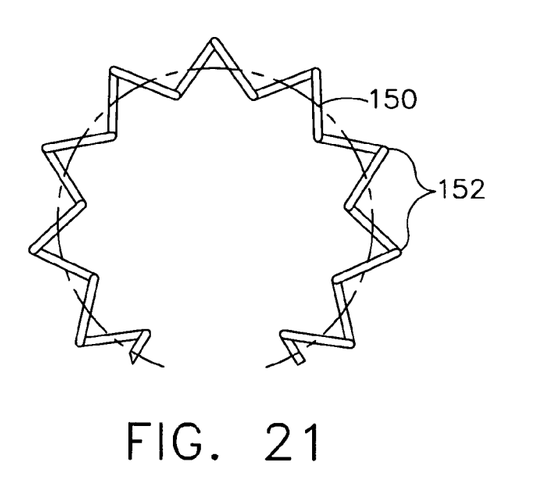
FIG. 21 is a side view of a fifth aspect of a surgical fastener.

As shown in FIG. 21, a surgical fastener 150 may include a plurality of coils 152 and may have a generally circular configuration (i.e., the fastener axis may be curved or non-linear).

Figure 22:
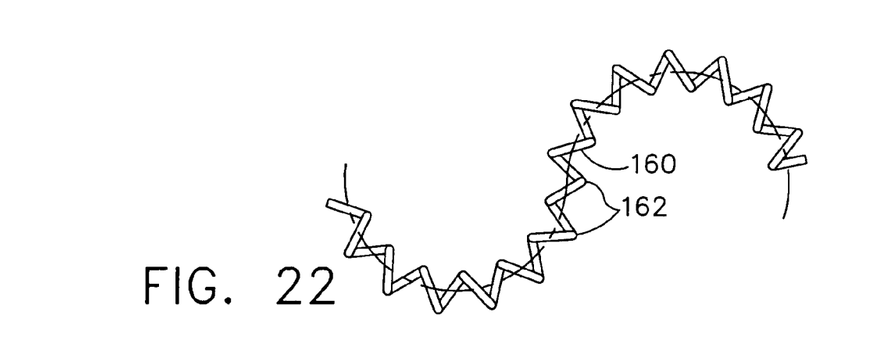
FIG. 22 is a side view of a sixth aspect of a surgical fastener.

As shown in FIG. 22, a surgical fastener 160 may include a plurality of coils 162 and may have a generally S-shaped configuration (i.e., the fastener axis may be generally S-shaped).

Figure 23:
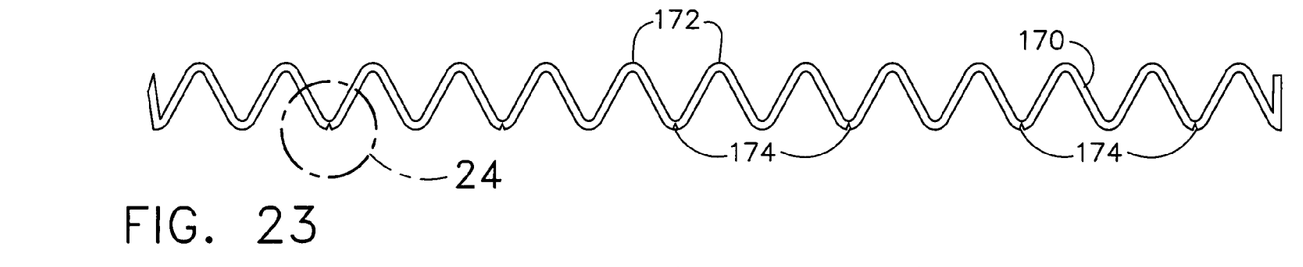
FIG. 23 is a side view of a seventh aspect of a surgical fastener.
Figure 24:
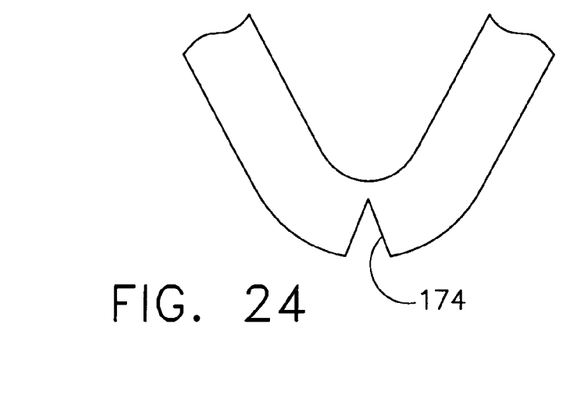
FIG. 24 is a detailed view of the surgical fastener shown in FIG. 23.

In another aspect, as shown in FIGS. 23 and 24, a surgical fastener 170 may be formed from a plurality of coils 172, wherein the coils may include break-points 174. The break points 174 may be easily broken either while in the instrument or after implantation in tissue. Each break-point 174 may be a weakened area of the fastener material, such as an indentation. The fastener 170 may facilitate the design of a multiple fastener deploying instrument or may provide the ability to deploy fasteners of varying lengths from a single instrument by incorporating a user-operated shearing mechanism, for example, in the distal end of the instrument.

In another aspect, the surgical fasteners disclosed herein may include a straight filament of fastener material, such as a titanium alloy wire that is formed into the helical shape in the end effector during deployment. The filament may be forced distally through a channel in the shaft by a pushing element or other deployment mechanism operatively engaged to an actuator on the handle. As the filament is driven into the fastening zone of the end effector, the filament may be formed into the coiled shape as the filament winds through tissue clamped between the end effector jaws. The length of the filament may range from a length sufficient to form one surgical fastener to a continuous filament pulled from a spool in the handle. For the latter situation, a cutting mechanism may be provided in the handle or shaft to automatically cut lengths of filament as needed prior to or during actuation of the deployment mechanism.

In general, with respect to the instruments and fasteners described and claimed herein, a user may operate the first actuator to hold tissue along the longitudinal axis in the tissue holding portion. The user may then operate the second actuator to drive the surgical fastener from the loaded position to the deployed position in the tissue holding portion of the end effector, thereby screwing the surgical fastener into tissue held in the tissue holding portion. The user may then operate the first actuator to change the end effector to the opened configuration, thereby releasing the tissue containing the surgical fastener.

Although various aspects of fasteners and instruments have been shown and described herein, it should be understood that modifications may occur to those skilled in the art. The disclosed fasteners and instruments include such modifications and are limited only by the scope of the claims.

What is claimed is:

1. A surgical fastener system comprising:
   an end effector including first and second opposable jaws movable between an open position and a closed position to clamp tissue therebetween when in said closed position, said first jaw including a first partial thread portion and said second jaw including a second partial thread portion, wherein said first partial thread portion cooperates with said second partial thread portion to define a full screw thread when said first and second jaws are in said closed position;
   a fastener positionable within said end effector, said fastener including a filament formed into a plurality of generally helical coils extending about a fastener axis, wherein a proximal end of said filament includes an engagement member and a distal end of said filament includes a penetrating tip; and
   a drive element adapted to engage said engagement member and rotate said fastener about said fastener axis to advance said fastener through said full screw thread.

2. The surgical fastener system of claim 1 wherein said full screw thread has an inner diameter that is generally larger than an outer diameter of said plurality of generally helical coils.

3. The surgical fastener system of claim 1 wherein said full screw thread has an inner diameter that is generally smaller than an outer diameter of said plurality of generally helical coils.

4. The surgical fastener system of claim 1 wherein said end effector is curved.

5. The surgical fastener system of claim 1 wherein a period of said full screw thread is approximately twice a period of said generally helical coils.

* * * * *